United States Patent
Busch et al.

(10) Patent No.: US 6,727,384 B1
(45) Date of Patent: Apr. 27, 2004

(54) METHOD FOR PURIFYING ACID CHLORIDES

(75) Inventors: Ralph Busch, Worms (DE); Heinz-Josef Kneuper, Niederkirchen (DE); Theodor Weber, Ludwigshafen (DE); Winfried Müller, Mannheim (DE); Armin Stamm, Mainz (DE); Jochem Henkelmann, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 108 days.

(21) Appl. No.: 10/070,762

(22) PCT Filed: Aug. 31, 2000

(86) PCT No.: PCT/EP00/08514

§ 371 (c)(1),
(2), (4) Date: Mar. 12, 2002

(87) PCT Pub. No.: WO01/19767

PCT Pub. Date: Mar. 22, 2001

(30) Foreign Application Priority Data

Sep. 13, 1999 (DE) .......................................... 199 43 858

(51) Int. Cl.$^7$ .............................................. C07C 51/58
(52) U.S. Cl. ...................................... 562/846; 562/866
(58) Field of Search ................................. 562/846, 866

(56) References Cited

U.S. PATENT DOCUMENTS

| | | |
|---|---|---|
| 4,900,479 A | 2/1990 | Freudenberg et al. |
| 5,166,427 A | 11/1992 | Hohmann et al. |
| 5,200,560 A | 4/1993 | Kanl et al. |
| 5,245,063 A | 9/1993 | Ksoll et al. |
| 5,430,186 A | 7/1995 | Ksoll et al. |

FOREIGN PATENT DOCUMENTS

| | | |
|---|---|---|
| DE | 43 37 785 | 5/1995 |
| DE | 199 43 844 | 3/2001 |
| EP | 0 296 404 | 12/1988 |
| EP | 0 367 050 | 5/1990 |
| EP | 0 452 806 | 10/1991 |
| EP | 0 475 137 | 3/1992 |
| EP | 0 635 473 | 1/1995 |

OTHER PUBLICATIONS

Ansell "Preparation of Acyl Halides" (1972) pp. 35–68.
Bosshard et al. "Eline Methode zur katalysierten Herstellung von Carbonsäure–und Sulfosäure–chloriden mit Thionylchlorid[1]" Helvetic Chimica Acta vol. XLII, (1959) pp. 1653–1658.
Pizey et al. "Synthetic Reagents" vol. 1, Chapter 4, (1974) pp. 321–357.

*Primary Examiner*—Paul J. Killos
(74) *Attorney, Agent, or Firm*—Keil & Weinkauf

(57) ABSTRACT

Process for the purification of carbonyl chlorides which have been prepared by reacting carboxylic acids with phosgene or thionyl chloride in the presence of a catalyst adduct, in which the carbonyl chlorides are treated with a hydrohalide of carboxamides of the formula (I)

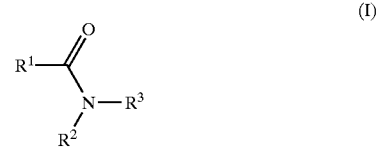

(I)

in which $R^1$ is hydrogen or $C_1$- to $C_3$-alkyl; $R^2$ and $R^3$ independently of one another are $C_1$- to $C_4$-alkyl, or $R^2$ and $R^3$ together are a $C_4$- or $C_5$-alkylene chain, and the carbonyl chloride purified in this way is isolated by separation off from the carboxamide hydrohalide phase.

9 Claims, No Drawings

METHOD FOR PURIFYING ACID CHLORIDES

The present invention relates to a process for the purification of carbonyl chlorides which originate from the reaction of the corresponding carboxylic acids with phosgene or thionyl chloride, which leads to carbonyl chlorides with an improved color number.

Carbonyl chlorides are important intermediates in the synthesis of a large number of chemical products, in particular pharmaceuticals, cosmetics, surfactants and paper auxiliaries. They can be prepared by reacting carboxylic acids with chlorinating agents, such as $PCl_3$, $POCl_3$, $SOCl_2$, $SO_2Cl_2$ or $COCl_2$. Of industrial importance are, in particular, the reactions with thionyl chloride, phosphorus trichloride and phosgene.

As a rule, in the synthesis via phosphorus trichloride, one reactant (carboxylic acid or phosphorus trichloride) is initially introduced, and the other reactant (phosphorus trichloride or carboxylic acid) is slowly added. Where appropriate, the synthesis is carried out in a solution diluted with a reaction-inert solvent (e.g. toluene). After removal of the phosphorous acid formed, the carbonyl chloride is as a rule purified by distillation. The addition of a catalyst is not required.

EP-A-0 296 404 describes the purification of crude carbonyl chlorides which originate from the chlorination using phosphorus trichloride, in which the reaction products are treated with carboxamide hydrohalides. The crude carbonyl chloride solutions from the phosphorus trichloride route differ in composition from those obtainable by the phosgene or thionyl chloride route. For example, the latter have:

(i) a considerably higher content of undesired minor components.

(ii) a varying composition of the minor components, which is influenced by the choice of chlorinating agent.

(iii) supplementary to the varying composition of the minor components, also the presence of degradation and/or secondary products from the catalyst adducts used.

The use of phosgene or thionyl chloride instead of phosphorus trichloride generally leads to a higher conversion and better selectivity. Both chlorinating agents additionally have the advantage over phosphorus trichloride that only gaseous byproducts are formed, which either escape in the form of gas during the synthesis or can be completely expelled by stripping with an inert gas when the reaction is complete. Furthermore, phosgene, in particular, is a very good value chlorinating agent.

Thionyl chloride and, in particular, phosgene are less reactive as chlorinating agents compared with phosphorus trichloride. The preparation of carbonyl chlorides by reacting carboxylic acids with thionyl chloride is therefore preferably carried out in the presence of a catalyst to increase the reaction rate. In the preparation by reaction with phosgene, a catalyst is always used. Catalyst precursors which are suitable for both chlorinating agents are N,N-disubstituted formamides and hydrochlorides thereof, and also pyridine or urea. Overviews relating to the chlorination by means of thionyl chloride are given in M. F. Ansell in S. Patai, "The Chemistry of Acyl Halides", John Wiley and Sons, New York 1972, 35–69 and H. H. Bosshard et al., Helv. Chem. Acta 62 (1959) 1653–1658 and S. S. Pizey, Synthetic Reagents, Vol. 1, John Wiley and Sons, New York 1974, ISBN 853120056, 321–557, in particular 333–335. Both by the phosgene route and also by the thionyl chloride route preference is given to using N,N-disubstituted formamides. These react with said chlorinating agents to give the Vilsmeier salts.

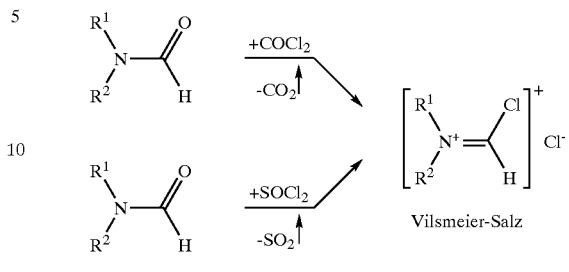

Vilsmeier-Salz

The Vilsmeier salt, the actual reactive chlorinating reagent, reacts with the carboxylic acid or the carboxylic anhydride to give the acid chloride. In the process, formamide-hydrochloride is reformed, which can in turn react with phosgene or thionyl chloride to give the Vilsmeier salt and passes through further catalyst circuits. The N,N-disubstituted formamide-hydrochlorides or Vilsmeier salts thereof are not, however, very thermally stable, meaning that it is possible for secondary reactions to take place above 80 to 90° C.

The preferred use of N,N-disubstituted formamides as catalyst precursor for the phosgenation of carboxylic acids also emerges from EP-A-0 367 050, EP-A-0 452 806, DE-A-4 337 785, EP-A-0 475 137 and EP-A-0 635 473.

As regards the color number, in the chlorination of carboxylic acids using phosgene or thionyl chloride, the use of catalysts has an adverse effect. Although these catalysts are separated off by phase separation following the chlorination, they can, however, remain in the product in small amounts and lead either themselves or as degradation or secondary products to yellow colorations of the carbonyl chlorides. For this reason, the carbonyl chlorides prepared via phosgene or thionyl chloride are generally purified by distillation to give largely colorless products. Such a distillation is not only an energy- and time-consuming operation, but also harbors a number of further disadvantages. Many longer-chain carbonyl chlorides cannot be distilled without partial decomposition. Furthermore, it is known that the distilled products can become contaminated as a result of decomposition of the catalyst still present in the distillation bottoms. Relatively large amounts of accumulated catalyst residue also represent a safety risk during the distillation since at elevated temperature there is the risk of spontaneous decomposition.

A further method of purifying the crude carbonyl chlorides is the treatment with activated carbons. However, these absorptive purification steps are industrially complex and, moreover, are not always successful. In addition, a contaminated solid forms, which has to be subsequently disposed of in the correct manner.

It is an object of the invention to develop a process for the purification of carbonyl chlorides which for the most part originate from the reaction of carboxylic acids with phosgene or thionyl chloride, which no longer has the known disadvantages and leads to carbonyl chlorides having an improved color number.

Surprisingly, we have found that this object is achieved by the development of a process for the purification of carbonyl chlorides which have been prepared by reacting carboxylic acids with phosgene or thionyl chloride in the presence of a catalyst adduct, which comprises treating the carbonyl chlorides with a hydrohalide of carboxamides of the formula (I)

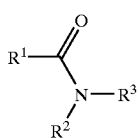

in which $R^1$ is hydrogen or a $C_1$- to $C_3$-alkyl; $R^2$ and $R^3$ independently of one another are $C_1$- to $C_4$-alkyl, or $R^2$ and $R^3$ together are a $C_4$- or $C_5$-alkylene chain, and isolating the carbonyl chloride purified in this way by separation from the carboxamide hydrohalide phase.

Contaminated carbonyl chlorides which originate from the reaction of carboxylic acids with phosgene or thionyl chloride can be worked up by extraction in high yield and with improved color number by the process according to the invention. The term "improved color number" is, in the case of the first treatment of the crude solutions, a reduction in the APHA color number to less than 50% of the original value for saturated carbonyl chlorides, and a reduction in the iodine color number to less than 75% of the original value for unsaturated carbonyl chlorides. The determinations of the APHA color number and of the iodine color number are described in the standard DIN EN 1557 (March 1997).

The treatment of the crude carbonyl chloride solution can be both spatially and also temporally separate from the synthesis of the crude solution. The treatment with a hydrohalide of carboxamides of the formula (I) can thus also be carried out in a different apparatus from the synthesis of the carbonyl chloride. Although synthesis and treatment of the crude carbonyl chloride solution can take place directly following one another in terms of time, it is also possible that they are temporally separated by hours, days, months or years, meaning that interim storage or transportation of the crude solution is also included.

For treatment of the crude carbonyl chloride solution by the process according to the invention, the solution is admixed, in an apparatus, which can also be identical to the reaction apparatus used above, with a hydrohalide of carboxamides of the formula (I)

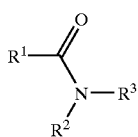

in which the substituents have the following meanings:
  $R^1$ is hydrogen or $C_1$- to $C_3$-alkyl, specifically methyl, ethyl, propyl or 1-methylethyl; particularly preferably hydrogen;
  $R^2$ and $R^3$ independently of one another are a $C_1$- to $C_4$-alkyl, specifically methyl, ethyl, propyl, 1-methylethyl, butyl, 1-methylpropyl, 2-methylpropyl or 1,1-dimethylethyl, or together are a $C_4$- or $C_5$-alkylene chain, specifically $CH_2CH_2CH_2CH_2$ or $CH_2CH_2CH_2CH_2CH2$; particularly preferably methyl.

It is essential that the mutual solubility of the carbonyl chlorides and hydrobalides of the carboxamides (I) is low and that two isolatable phases form.

The amount of hydrohalides of the carboxamides (I) to be added is dependent on various factors, but primarily on the type of carbonyl chloride itself and the amount of secondary components present in the crude carbonyl chloride solution, which in turn are evident from the coloration. Based on the amount of the carbonyl chloride, from 1 to 80% by weight, preferably from 2 to 60% by weight and particularly preferably from 5 to 50% by weight of hydrohalide of the carboxamides (I) are in general to be used.

The hydrohalide of the carboxamides (I) used is preferably the hydrochloride, particularly preferably the hydrochloride of N,N-dimethylformamide. The molar fraction of hydrochloride (as HCl), based on the N,N-dimethylformamide, is in the range between 0.1 and 2.5. Preference is given to using a molar fraction of from 1.0 to 2.0.

The preparation of the carboxamide hydrohalides from carboxamides (I) and hydrohalide can be carried out either before the addition of the carbonyl chloride or after its addition.

The treatment of the crude carbonyl chloride solution with the hydrohalides of the carboxamides (I) is preferably carried out at a temperature of from −15 to 80° C., preferably −10 to 40° C., particularly preferably at 0 to 30° C., and a pressure from 0.5 to 5 bar abs, preferably 0.8 to 1.2 bar abs, with vigorous mixing. The parameters to be set depend here on the desired residual content of carboxamide hydrohalide in the carbonyl chloride phase and, for each system, is to be matched to the procedures known to the person skilled in the art. The time period depends essentially on the solubility of the undesired secondary components in the carboxamide hydrohalide phase and is likewise to be determined for the particular system. Generally, vigorous mixing is carried out for one hour at most.

The treatment can be carried out either batchwise or continuously.

(a) Batchwise Treatment:
  In the batchwise treatment, the crude carbonyl chloride solution and the carboxamide hydrohalide phase are combined in an apparatus, and the system is vigorously mixed as described above. Suitable apparatuses are, for example, stirred tank reactors or phase-separating vessels ("mixer settlers"). When mixing is complete, the two phases are separated. This can be carried out in the treatment or mixing apparatus which is already being used or in a separate apparatus, for example a separating vessel. Generally, the two phases have separated after two hours at most and can then be isolated.

(b) Continuous Treatment:
  In the continuous treatment, the crude carbonyl chloride solution and the carboxamide hydrohalide phase are fed continuously to a treatment or mixing apparatus. The treatment can be carried out in a known manner in stirred tank reactors, batteries of stirred tank reactors, static mixers, phase-separating vessels ("mixer settlers") or liquid-liquid extraction columns (see Ullmann's Encyclopedia of Industrial Chemistry, 6th edition, 1998, Electronic Release, Liquid-liquid-extraction). An amount corresponding to the amount of both phases introduced is continuously drawn off from the treatment or mixing apparatus. Here, it must be ensured that the ratio between carbonyl chloride and carboxamide hydrohalide remains virtually constant. The amount removed is fed to another apparatus, for example a separating vessel for separation of the two phases. In this connection, it is also possible for a settling zone to be inserted between treatment or mixing apparatus and separating vessel. The two phases can be removed separately from the separating vessel.

To separate off the carboxamide-hydrohalide-containing phase, it is also possible to use suitable filters, such as, for example, coalescence filters of known design. The separated-off carboxamide-hydrohalide-containing phase can optionally be reused for the extraction, the amount of hydrohalide passed over into the carbonyl chloride phase advantageously being replaced.

The carbonyl chloride solutions treated in this way have an improved color number compared to untreated solutions and can then either be used directly for further synthesis stages or, if required, be subjected to still further treatment procedures. In this regard, renewed treatment with a hydrohalide of carboxamides (I) by the process according to the invention, distillation or adsorptive purification may be mentioned without limitation.

In a further embodiment, the separated-off carboxamide hydrohalide phase is subsequently used as catalyst precursor for the formation of the catalyst adduct of phosgene or thionyl chloride and the N,N-disubstituted formamide. For this, the separated-off carboxamide hydrohalide phase is treated with phosgene or thionyl chloride in order to subsequently use it as a catalyst adduct.

Carbonyl chlorides which can be prepared by the process according to the invention are, for example, those of the formula (III)

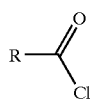

(III)

in which R stands for the following radicals:

$C_1$- to $C_{30}$-alkyl or their aryl- or cycloalkyl-substituted components:
saturated, straight-chain or branched hydrocarbon radical having from 1 to 30 carbon atoms, preferably methyl, ethyl, propyl, 1-methylethyl, butyl, 1-methylpropyl, 2-methylpropyl, 1,1-dimethylethyl, pentyl, 1-ethylpropyl, hexyl, heptyl, 1-ethylpentyl, octyl, 2,4,4-trimethylpentyl, nonyl, 1,1-dimethylheptyl, decyl, undecyl, dodecyl, tridecyl, tetradecyl, pentadecyl, hexadecyl, heptadecyl, octadecyl, nonadecyl, icosyl, henicosyl, docosyl, tricosyl, tetracosyl, pentacosyl, hexacosyl, heptacosyl, octacosyl, nonacosyl, triacontyl, phenylmethyl, diphenylmethyl, triphenylmethyl, 2-phenylethyl, 3-phenylpropyl, cyclopentylmethyl, 2-cyclopentylethyl, 3-cyclopentylpropyl, cyclohexylmethyl, 2-cyclohexylethyl, 3-cyclohexylpropyl;

$C_3$- to $C_{12}$-cycloalkyl or their aryl- or cycloalkyl-substituted components:
monocyclic, saturated hydrocarbon radical having from 3 to 12 ring carbon atoms, preferably cyclopentyl, cyclohexyl;

$C_2$- to $C_{30}$-alkenyl or their aryl- or cycloalkyl-substituted components:
unsaturated, straight-chain or branched hydrocarbon radical having from 1 to 30 carbon atoms and 1 to 5 double bonds at any position, preferably 2-propenyl, 3-butenyl, cis-2-butenyl, trans-2-butenyl, cis-8-heptadecenyl, trans-8-heptadecenyl, cis,cis-8,11-heptadecadienyl, cis,cis,cis-8,11,14-heptadecatrienyl;

$C_3$- to $C_{12}$-cycloalkenyl or their aryl- or cycloalkyl-substituted components:
monocyclic, unsaturated hydrocarbon radical having from 3 to 12 ring carbon atoms and 1 to 3 double bonds at any position, preferably 3-cyclopentenyl, 2-cyclohexenyl, 3-cyclohexenyl, 2,5-cyclohexadienyl;

$C_2$- to $C_{30}$-alkynyl or their aryl- or cycloalkyl-substituted components:
unsaturated, straight-chain or branched hydrocarbon radical having from 1 to 30 carbon atoms and 1 to 3 triple bonds at any position, preferably 3-butynyl, 4-pentynyl;

$C_4$- to $C_{30}$-alkenynyl or their aryl- or cycloalkyl-substituted components:
unsaturated, straight-chain or branched hydrocarbon radical having from 1 to 30 carbon atoms, 1 to 3 triple bonds and 1 to 3 double bonds at any position.

Using the process according to the invention, it is also possible to prepare mixtures of said carbonyl chlorides. Non-limiting examples which may be mentioned are mixtures comprising $C_8$- to $C_{18}$-carbonyl chlorides, which are traded under the trivial names "carboxylic acid chloride", "tallow fatty acid chloride", "coconut fatty acid chloride" and "oleic acid chloride".

Particular preference is given to preparing carbonyl chlorides of the formula (III) by the process according to the invention in which R stands for the following radicals:

$C_1$- to $C_{30}$-alkyl or their aryl- or cycloalkyl-substituted components:
saturated, straight-chain or branched hydrocarbon radical having from 1 to 30 carbon atoms, preferably methyl, ethyl, propyl, 1-methylethyl, butyl, 1-methylpropyl, 2-methylpropyl, 1,1-dimethylethyl, pentyl, 1-ethylpropyl, hexyl, heptyl, 1-ethylpentyl, octyl, 2,4,4-trimethylpentyl, nonyl, 1,1-dimethylheptyl, decyl, undecyl, dodecyl, tridecyl, tetradecyl, pentadecyl, hexadecyl, heptadecyl, octadecyl, nonadecyl, icosyl, henicosyl, docosyl, tricosyl, tetracosyl, pentacosyl, hexacosyl, heptacosyl, octacosyl, nonacosyl, triacontyl, phenylmethyl, diphenylmethyl, triphenylmethyl, 2-phenylethyl, 3-phenylpropyl, cyclopentylmethyl, 2-cyclopentylethyl, 3-cyclopentylpropyl, cyclohexylmethyl, 2-cyclohexylethyl, 3-cyclohexylpropyl;

$C_2$- to $C_{30}$-alkenyl or their aryl- or cycloalkyl-substituted components:
unsaturated, straight-chain or branched hydrocarbon radical having from 1 to 30 carbon atoms and 1 to 5 double bonds at any position, preferably 2-propenyl, 3-butenyl, cis-2-butenyl, trans-2-butenyl, cis-8-heptadecenyl, trans-8-heptadecenyl, cis,cis-8,11-heptadecadienyl, cis,cis,cis-8,11,14-heptadecatrienyl; and mixtures thereof.

Very particularly preferably, the process according to the invention is used to prepare acetyl chloride (R=methyl), propionyl chloride (R=ethyl), butyryl chloride (R=propyl), valeryl chloride (R=butyl), isovaleryl chloride (R=2-methylpropyl), pivaloyl chloride (R=1,1-dimethylethyl), caproyl chloride (R=pentyl), 2-ethylbutyryl chloride (R=1-ethylpropyl), enanthyl chloride (R=hexyl), capryloyl chloride (R=heptyl), 2-ethylhexanoyl chloride (R=1-ethylpentyl), pelargonoyl chloride (R=octyl), isononanoyl chloride (R=2,4,4-trimethylpentyl), capryl chloride (R=nonyl), neodecanoyl chloride (R=1,1-dimethylheptyl), lauroyl chloride (R=undecyl), myristoyl chloride (R=tridecyl), palmitoyl chloride (R=pentadecyl), stearoyl chloride (R=heptadecyl), oleoyl chloride (R=cis-8-heptadecenyl), linoleoyl chloride (R=cis,cis-8,11-heptadecadienyl), linolenoyl chloride (R=cis,cis,cis-8,11,14-heptadecatrienyl), arachidoyl chloride (R=nonadecyl) and behenoyl chloride (R=henicosyl) and mixtures thereof.

The carboxylic acids according to formula (III) to be used advantageously for the process according to the invention arise from the above-described definitions for R.

In the preparation of the crude carbonyl chloride solution, the catalyst used is a catalyst adduct which originates from the reaction of phosgene or thionyl chloride with an N,N-disubstituted formamide. The latter, which is also referred to as a catalyst precursor, is defined by the formula (II)

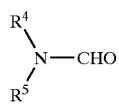

(II)

in which $R^4$ and $R^5$ independently of one another are a $C_1$- to $C_4$-alkyl, specifically methyl, ethyl, propyl, 1-methylethyl, butyl, 1-methylpropyl, 2-methylpropyl and 1,1-dimethylethyl, or together are a $C_4$- or $C_5$-alkylene chain, specifically $CH_2CH_2CH_2CH_2$ or $CH_2CH_2CH_2CH_2CH_2$. Preference is given to using N,N-dimethylformamide.

The preparation of the carbonyl chlorides to be used in the process according to the invention from the reaction of carboxylic acids with phosgene or thionyl chloride is carried out by prior art processes which are generally known.

The formation of the catalyst adduct can either be carried out in the apparatus in which the chlorination is carried out, or else upstream in another apparatus. In the last-mentioned case, a certain amount of the N,N-disubstituted formamide is introduced into a separate apparatus, mixed with the desired amount of phosgene or thionyl chloride and then passed to the actual reaction apparatus. In the first-mentioned case, the procedure described is carried out directly in the reaction apparatus.

The reaction of the carboxylic acids with phosgene or thionyl chloride in the presence of the catalyst adduct described can be carried out either batchwise or continuously. In the phosgene variant, a molar ratio between the catalyst adduct and the carboxylic acid of from 0.05 to 2.0, preferably from 0.1 to 1.0, particularly preferably from 0.1 to 0.3, is to be set, and in the thionyl chloride variant, a molar ratio of from 0.001 to 0.05, preferably from 0.001 to 0.01, is to be set. In both variants, the reaction is carried out at temperatures between 20 and 100° C., preferably between 30 and 80° C., particularly preferably between 30 and 70° C., and a pressure between 0.5 and 2.0 bar abs, preferably from 0.8 to 1.2 bar abs, particularly preferably at atmospheric pressure. The total amount of phosgene or thionyl chloride added is from 1.0 to 2.0 of the molar amount of the carboxylic acid used, preferably from 1.0 to 1.3 of the molar amount of the carboxylic acid used.

(a) Batchwise Preparation:

In the batchwise preparation, the reaction mixture, consisting of a carboxylic acid and the catalyst adduct, prepared from phosgene or thionyl chloride and the N,N-disubstituted formamide of the formula (II), is introduced into a reaction apparatus, for example a stirred tank reactor, and brought to the reaction temperature and, where necessary, to the reaction pressure. Then, the desired amount of liquid or gaseous phosgene or thionyl chloride is added over a certain period of time. The time requirement for the addition of the chlorinating agent depends on the rate of the reaction and can generally be limited to a few hours. The reaction solution is then generally left to stand for 1 to 2 hours, and the two phases are separated from one another. As a rule, the carbonyl-chloride-containing phase is the upper phase, and the catalyst-adduct-containing phase is the lower phase.

(b) Continuous Preparation:

Reaction apparatuses suitable for the continuous procedure are, for example, stirred tank reactors, batteries of stirred tank reactors or reaction columns operated countercurrently. Using a stirred tank reactor, the carboxylic acid and the catalyst adduct, prepared from phosgene or thionyl chloride and the N,N-disubstituted formamide of the formula (II), are initially introduced, the desired reaction temperature and optionally the desired reaction pressure are set, and liquid or gaseous phosgene or thionyl chloride is added. After an amount of chlorinating agent approximately equivalent to the carboxylic acid has been introduced, the simultaneous introduction of carboxylic acid and catalyst adduct, and also an amount of phosgene or thionyl chloride which is essentially equimolar to the introduced carboxylic acid, is started. An amount of the reaction volume corresponding to the introduced reactants is drawn off from the reaction apparatus, for example via a level control, and passed to a separating vessel. In the separating vessel, the carbonyl chloride of the formula (III), as upper phase, can be continuously drawn off, and the catalyst adduct, as the lower phase, can be continuously returned to the reactor. In carrying out the reaction, it must be ensured that the chlorinating agent entrained by the reaction exit gases is replaced by introducing additional chlorinating agent.

The catalyst phase can be separated off at temperatures of from −15° C. to 40° C., preferably −10 to 30° C., particularly preferably −5 to 20° C. The upper, carbonyl-chloride-containing phase is referred to below as the crude carbonyl chloride solution. To separate off the catalyst phase it is also possible to use suitable filters, such as, for example, coalescence filters of known design.

The process according to the invention does not rule out the possibility of also adding carboxylic acids of another origin to a low extent.

Preferably, the carbonyl chlorides according to Formula (III) used for the purification are for the most part obtained from the reaction of the corresponding carboxylic acids with phosgene in the presence of the catalyst adduct described.

In a general variant for the batchwise preparation of the crude carbonyl chloride solution by reacting the carboxylic acid with phosgene, the catalyst adduct, which can be obtained by introducing phosgene into N,N-disubstituted formamide, is initially introduced into a stirred tank reactor, and carboxylic acid is added thereto. After the desired reaction conditions temperature and optionally pressure have been set, the amount of gaseous or liquid phosgene required for the reaction is continuously introduced with stirring over the course of the desired period. When the reaction is complete, the contents of the stirred tank reactor are transferred to a separating vessel for phase separation. The stirred tank reactor is then available for a further reaction batch. After about 1 to 2 hours the two phases have clearly separated from one another. The lower phase, which is generally the catalyst-containing phase, is separated off, and the carbonyl chloride phase, which is referred to as the crude carbonyl chloride solution, is isolated.

In a general variant for the batchwise purification, the crude carbonyl chloride solution is transferred to a stirred tank reactor, carboxamide is added, and the desired amount of hydrohalide is introduced with stirring. In the process, a second phase forms, which consists predominantly of the carboxamide hydrohalide. Alternatively, it is also possible to add carboxamide hydrohalide which has been prepared separately. In this second, carboxamide-hydrohalide-containing phase, the undesired, color-imparting secondary components of the carbonyl chloride are dissolved with stirring. By switching off the stirrer or transferring the mixture to a further separating vessel the two phases are separated. The carbonyl-chloride-containing phase can then, if necessary, be subjected to further purification, for example by renewed extraction with carboxamide hydrohalide, or to removal of dissolved hydrohalide, for example by stripping with inert gas, such as, for example, nitrogen or argon, or by evacuation. The carboxamide-hydrohalide-containing phase can optionally be reused for the extraction. If an N,N-disubstituted formamide is used which is identical to the catalyst precursor, then charging with phosgene and subsequent use as catalyst adduct in the carbonyl chloride synthesis can also take place. At the same time, partial discharge is also possible to remove the accumulated, color-imparting impurities. The discharged carboxamide-hydrohalide-containing phase can, furthermore, also be disposed of or purified by distillation to remove the impurities.

In a further general variant for the continuous preparation of the crude carbonyl chloride solution by reacting the carboxylic acid with phosgene, the carboxylic acid, recycled catalyst adduct and gaseous or liquid phosgene are continuously fed to a stirred tank reactor under the desired reaction conditions with stirring. An amount corresponding to the introduced amount is continuously drawn off from the stirred tank reactor and passed to a separating vessel. From this, the catalyst-containing phase, which is usually at the bottom, is continuously separated off and returned to the stirred tank reactor. For removal of impurities, it is advantageous to bleed out a small fraction between 1 and 10% by weight and to replace it by fresh catalyst precursor. The crude carbonyl chloride solution is likewise continuously drawn off from the separating vessel.

In a further general variant for the continuous purification, the crude carbonyl chloride solution is passed for extraction to a battery of stirred tank reactors, with, for example, two stirred tank reactors. In parallel to the introduction of the crude carbonyl chloride solution, recycled carboxamide hydrohalide is added to the first stirred tank reactor. To replace discharged hydrohalide, gaseous hydrohalide is introduced into the first stirred tank reactor. After passing through the individual battery stages, the runoff from the last stirred tank reactor passes to a separating vessel, where the two phases separate from one another. The carbonyl-chloride-containing phase is continuously drawn off and further processed as described under the batchwise variant. The carboxamide-hydrohalide-containing phase is likewise continuously drawn off and returned to the first stirred tank reactor. To remove the extracted impurities, it is advantageous to bleed out a fraction between 1 and 20% by weight and replace it with fresh carboxamide or its hydrohalide.

An essential feature in the treatment of the crude carbonyl chloride solution according to the invention and described above is the surprising effect that precisely the color-imparting components are considerably more soluble in the carboxamide-hydrohalide-containing phase than in the carbonyl-chloride-containing phase.

The process according to the invention leads, mainly as a result of a single extraction, to a significant reduction in color number, meaning that the carbonyl chlorides purified in this manner can generally be used for subsequent reactions without distillation or adsorptive treatment. The process according to the invention can be carried out very effectively and economically. By avoiding the distillation which is customary according to the prior art, both investment and energy costs are saved, and also as a rule a higher yield of purified carbonyl chloride is achieved. For distillation-sensitive carbonyl chlorides, the process according to the invention opens up the possibility of an economical synthesis on an industrial scale.

EXAMPLES

Synthesis 1: Preparation of N,N-Dimethylformamide Hydrochloride

The synthesis of N,N-dimethylformamide hydrochloride is described in I. S. Kislina et al., Russ. Chem. Bl., EN, 43(9), 1994, 1505–1507. 365.5 g (5.0 mol) of N,N-dimethylformamide (DMF) were introduced into a stirred apparatus and heated to 45° C. Then, with stirring, gaseous HCl is introduced until the onset of an amount of exit gas. This gave a clear, colorless liquid which corresponded, according to the elemental analysis, to a composition of DMF*2HCl.

Process 1: Batchwise Preparation of the Crude Carbonyl Chloride Solution via Phosgene For the preparation of the crude carbonyl chloride solutions by a batchwise process, in each case 2 to 5 mol of the corresponding carboxylic acids were introduced into a stirred apparatus, and 10 to 50 mol %, based on the carboxylic acid used, of N,N-dimethylformamide were added thereto. The reaction solution was brought, with stirring, to a temperature of from 25 to 45° C., and gaseous phosgene was introduced under atmospheric pressure. After the stoichiometric amount (based on the amount of carboxylic acid introduced) of phosgene, including the desired excess, had been introduced, the further introduction was stopped, and the system was left to stand for 2 hours with the stirrer switched off. Following separation of the two phases, the crude carbonyl chloride solution, as the upper phase, was isolated and the APHA color number was determined.

Process 2: Continuous Preparation of the Crude Carbonyl Chloride Solution via Phosgene For the preparation of the crude carbonyl chloride solutions by a continuous process, in each case 0.75 mol/h of the corresponding carboxylic acids, 30 g/h of recycled catalyst adduct, and 0.75 to 0.80 mol/h of gaseous phosgene were introduced into a stirred apparatus at a temperature of 45° C. and a pressure of 1 bar abs. By means of the level control which was present, the corresponding amount of reaction mixture was drawn off and passed to a separating vessel. The lower, catalyst-containing phase was recycled. The upper, carbonyl-chloride-containing phase was isolated as crude carbonyl chloride solution and the APHA color number was determined.

Example 1

Purification of Lauroyl Chloride

Lauric acid and phosgene were used to prepare, by the batchwise process 1, a crude lauroyl chloride solution having a color number of 268 APHA. 200 g of this product were stirred vigorously with 50 g of DMF hydrochloride from synthesis 1 in a stirred apparatus, and then the phases were separated. The lauroyl chloride phase was stripped until HCl-free using nitrogen. The color number was then only 48 APHA.

Example 2

Purification of Coconut Fatty Acid Chloride

Coconut fatty acid (trade name HK 8-18, Henkel), which consists essentially of lauric acid and myristic acid, and phosgene were used to prepare, by the batchwise process 1, a crude coconut fatty acid chloride solution having a color number of 399 APHA. 200 g of this product were stirred vigorously with 50 g of DMF hydrochloride from synthesis 1 in a stirred apparatus and then the phases were separated. The coconut fatty acid chloride phase was stripped until HCl-free using nitrogen. The color number was then only 64 APHA.

Example 3

Purification of Pelargonoyl Chloride (Nonanoyl Chloride)

Pelargonic acid (nonanoic acid) and phosgene were used to prepare, by the continuous process 2, a crude pelargonoyl chloride solution having a color number of 301 APHA. 90 g of this product were stirred vigorously with 10 g of DMF hydrochloride from synthesis 1 in a stirred apparatus, and then the phases were separated. The pelargonoyl chloride phase was stripped until HCl-free using nitrogen. The color number was then only 55 APHA. Repetition of the extraction using a further 10 g of DMF hydrochloride from synthesis 1 led to a colour number of 36 APHA. After a third extraction which was carried out analogously, the color number was then only 30 APHA.

Example 4
Purification of Pelargonoyl Chloride (Nonanoyl Chloride)

Pelargonic acid (nonanoic acid) and phosgene were used to prepare, by batchwise process 1, a crude pelargonoyl chloride solution having a color number of 118 APHA. 90 g of this product were stirred vigorously with 10 g of DMF hydrochloride from synthesis 1 in a stirred apparatus, and then the phases were separated. The pelargonoyl chloride phase was stripped until HCl-free using nitrogen. The color number was then only 50 APHA. Repetition of the extraction with a further 10 g of DMF hydrochloride from synthesis 1 led to a color number of 48 APHA. After a third extraction, carried out in an analogous manner, the color number was 45 APHA.

Example 5
Purification of Pivaloyl Chloride

Pivalic acid and phosgene were used to prepare, by the continuous process 2, a crude pivaloyl chloride solution having a color number of 361 APHA. 200 g of this product were vigorously stirred with 50 g of DMF hydrochloride from synthesis 1 in a stirred apparatus, and then the phases were separated. The pivaloyl chloride phase was stripped until HCl-free using nitrogen. The color number was then only 35 APHA.

Example 6
Purification of Pivaloyl Chloride (Repetition)

Pivalic acid and phosgene were used to prepare, by the continuous process 2, a crude pivaloyl chloride solution having a color number of 409 APHA. 200 g of this product were vigorously stirred with 50 g of DMF hydrochloride from synthesis 1 in a stirred apparatus, and then the phases were separated. The pivaloyl chloride phase was stripped until HCl-free using nitrogen. The color number was then only 83 APHA.

Since, compared to Example 5, in the present example the starting crude solution had a higher color number, a purified solution with a higher color number was also obtained. The depletion of the color components is, however, comparable in the two examples.

Example 7
Purification of Oleoyl Chloride

Oleic acid and phosgene were used to prepare, by continuous process 2, a crude oleoyl chloride solution having an iodine color number of 38. 200 g of this product were vigorously stirred with 50 g of DMF hydrochloride from synthesis 1 in a stirred apparatus, and then the phases were separated. The oleoyl chloride phase was stripped until HCl-free using nitrogen. The iodine color number was then only 26.

Example 8
Purification of Palmitoyl Chloride

Palmitic acid and phosgene were used to prepare, by batchwise process 1, a crude palmitoyl chloride solution having a color number of 202 APHA. 20 ml of this product were vigorously stirred with 5 ml of DMF hydrochloride from synthesis 1 in a stirred apparatus, and then the phases were separated. The palmitoyl chloride phase was stripped until HCl-free using nitrogen. The color number was then only 82 APHA.

Example 9
Purification of Pelargonoyl Chloride (Nonanoyl Chloride)

0.4 g (0.005 mol) of N,N-dimethylformamide were added to 158 g (1.0 mol) of pelargonic acid, and the mixture was heated to 50° C. At 50° C., a total of 125 g (1.05 mol) of thionyl chloride were added dropwise over the course of 45 minutes. After a post reaction time of 30 minutes at 50° C., nitrogen was passed through the mixture at 50° C. for 1 hour, and sulfur dioxide, hydrogen chloride gas and unreacted thionyl chloride were stripped out. The pale yellow product had a color number of 113 APHA and, according to GC analysis, comprised 99.5 area % of pelargonoyl chloride.

20 ml of the product were vigorously stirred with 5 ml of DMF hydrochloride from synthesis 1 in a stirred apparatus, and then the phases were separated. The pelargonoyl chloride phase was stripped until HCl-free using nitrogen. The color number was then only 37 APHA.

The examples show for carbonyl chlorides from both synthesis routes, via phosgene and via thionyl chloride, that irrespective of the type of carboxylic acid, i.e. irrespective of whether the carboxylic acid is saturated or unsaturated, or straight-chain or branched, the color number can be significantly reduced as a result of the treatment (extraction) according to the invention. Repeated extraction leads to a further reduction in the color number. The carbonyl chlorides obtained in the examples can be used in subsequent syntheses without further purification steps.

We claim:

1. A process for the purification of carbonyl chlorides which have been prepared by reacting carboxylic acids with phosgene or thionyl chloride in the presence of a catalyst adduct, which comprises treating the carbonyl chlorides with a hydrohalide of carboxamides of the formula (I)

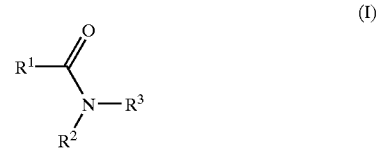

in which $R^1$ is hydrogen or a $C_1$- to $C_3$-alkyl; $R^2$ and $R^3$ independently of one another are $C_1$- to $C_4$-alkyl, or $R^2$ and $R^3$ together are a $C_4$- or $C_5$-alkylene chain, the mutal solubility of the carbonyl chlorides and the hydrohalides of the carboxamides (I) being low, and isolating the carbonyl chloride purified in this way by separation from the carboxamide hydrohalide phase.

2. A process as claimed in claim 1, wherein, for the treatment of the carbonyl chlorides, an amount of carboxamide hydrohalide of from 1 to 80% by weight, based on the amount of carbonyl chloride employed, is used.

3. A process as claimed in claim 1, wherein the carboxamide hydrohalide used is N,N-dimethylformamide hydrochloride.

4. A process as claimed in claim 1, wherein the treatment with the carboxamide hydrohalide is carried out at a temperature of from −15 to 80° C. and a pressure of from 0.5 to 5.0 bar abs.

5. A process as claimed in claim 1, wherein, as catalyst precursor for the catalyst adduct to be formed, an N,N- disubstituted formamide of the formula (II) is used

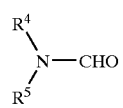
(II)

in which $R^4$ and $R^5$ independently of one another are $C_1$- to $C_4$-alkyl, or $R^4$ and $R^5$ together are a $C_4$- or $C_5$-alkylene chain.

6. A process as claimed in claim 1, wherein the catalyst precursor according to the formula (II) used is N,N-dimethylformamide.

7. A process as claimed in claim 3, wherein the N,N-dimethylformamide hydrochloride, after it has been used as treatment agent, is used as catalyst precursor in the carbonyl chloride synthesis.

8. A process as claimed in claim 1, wherein most of the carbonyl chlorides used originate from the reaction of carboxylic acids with phosgene in the presence of a catalyst adduct.

9. A process as claimed in claim 1, wherein the carbonyl chlorides to be purified are acetyl chloride, propionyl chloride, butyryl chloride, valeryl chloride, isovaleryl chloride, pivaloyl chloride, caproyl chloride, 2-ethylbutyryl chloride, enanthyl chloride, capryloyl chloride, 2-ethylhexanoyl chloride, pelargonoyl chloride, isononanoyl chloride, capryl chloride, neodecanoyl chloride, lauroyl chloride, myristoyl chloride, palmitoyl chloride, stearoyl chloride, oleoyl chloride, linoleoyl chloride, linolenoyl chloride, arachidoyl chloride and behenoyl chloride, and mixtures thereof.

\* \* \* \* \*